United States Patent
Nagashima et al.

(10) Patent No.: US 10,904,981 B2
(45) Date of Patent: Jan. 26, 2021

(54) MEDICAL LIGHT SOURCE SYSTEM, MEDICAL LIGHT SOURCE DEVICE, AND METHOD OF ADJUSTING LIGHT AMOUNT OF MEDICAL LIGHT SOURCE DEVICE

(71) Applicant: SONY CORPORATION, Tokyo (JP)

(72) Inventors: Zenya Nagashima, Kanagawa (JP); Tomoyuki Oki, Kanagawa (JP); Masayoshi Akita, Tokyo (JP); Hirotaka Muramatsu, Kanagawa (JP); Akio Furukawa, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/609,632

(22) PCT Filed: Feb. 16, 2018

(86) PCT No.: PCT/JP2018/005458
§ 371 (c)(1),
(2) Date: Oct. 30, 2019

(87) PCT Pub. No.: WO2018/207423
PCT Pub. Date: Nov. 15, 2018

(65) Prior Publication Data
US 2020/0154548 A1 May 14, 2020

(30) Foreign Application Priority Data
May 9, 2017 (JP) ................................. 2017-092847

(51) Int. Cl.
*H05B 47/10* (2020.01)
*A61B 90/30* (2016.01)
(Continued)

(52) U.S. Cl.
CPC ............ *H05B 47/10* (2020.01); *A61B 90/30* (2016.02); *A61B 1/063* (2013.01); *A61B 90/20* (2016.02)

(58) Field of Classification Search
CPC ......... H05B 47/10; A61B 90/30; A61B 90/20; A61B 1/063; A61B 1/06; F21S 2/00; F21V 23/00
See application file for complete search history.

(56) References Cited

U.S. PATENT DOCUMENTS

2006/0049782 A1 3/2006 Vornsand et al.
2007/0040512 A1* 2/2007 Jungwirth .............. H05B 45/20
315/159
(Continued)

FOREIGN PATENT DOCUMENTS

CN 1830096 A 9/2006
CN 104434000 A 3/2015
(Continued)

OTHER PUBLICATIONS

International Search Report and Written Opinion of PCT Application No. PCT/JP2018/005458, dated May 15, 2018, 09 pages of ISRWO.

*Primary Examiner* — Daniel D Chang
(74) *Attorney, Agent, or Firm* — Chip Law Group

(57) ABSTRACT

Provided is a medical light source device that includes a light source part including two or more semiconductor light-emitting devices having wavelengths of emitted light different from each other. The light source part generates light of predetermined chromaticity by mixing the light emitted from each of the semiconductor light-emitting devices and emits outward the generated light of the chromaticity as illumination light. The medical light source device further includes a control unit that controls a mixing rate of the light emitted from each of the semiconductor (Continued)

light-emitting devices based on a light amount setting value of the illumination light emitted from the light source part, and keeps the chromaticity constant regardless of a light amount of the illumination light.

10 Claims, 8 Drawing Sheets

(51) Int. Cl.
*A61B 1/06* (2006.01)
*A61B 90/20* (2016.01)

(56) References Cited

U.S. PATENT DOCUMENTS

| | | |
|---|---|---|
| 2007/0120496 A1 | 5/2007 | Shimizu et al. |
| 2014/0293432 A1 | 10/2014 | Takemoto |
| 2015/0087903 A1 | 3/2015 | Kuramoto |
| 2017/0074467 A1* | 3/2017 | Roth ................ A61N 5/06 |
| 2018/0062344 A1* | 3/2018 | Smith ................ G01J 1/4257 |

FOREIGN PATENT DOCUMENTS

| | | |
|---|---|---|
| EP | 1662583 A1 | 5/2006 |
| EP | 2784458 A1 | 10/2014 |
| EP | 2850994 A1 | 3/2015 |
| JP | 2014-197044 A | 10/2014 |
| JP | 2015-061569 A | 4/2015 |
| JP | 2015-106887 A | 6/2015 |
| JP | 2015-231553 A | 12/2015 |
| KR | 10-2006-0056348 A | 5/2006 |
| WO | 2005/011006 A1 | 2/2005 |

* cited by examiner

| LIGHT AMOUNT LEVEL | MIXING RATE | | |
|---|---|---|---|
| | SEMICONDUCTOR LIGHT-EMITTING DEVICE A | SEMICONDUCTOR LIGHT-EMITTING DEVICE B | . . . |
| 20 | 0.450 | 0.350 | . . . |
| 19 | 0.445 | 0.355 | . . . |
| ⋮ | ⋮ | ⋮ | ⋮ |

FIG. 4

| LIGHT AMOUNT LEVEL | MIXING RATE | | |
|---|---|---|---|
| | SEMICONDUCTOR LIGHT-EMITTING DEVICE 101R | SEMICONDUCTOR LIGHT-EMITTING DEVICE 101G | SEMICONDUCTOR LIGHT-EMITTING DEVICE 101B |
| 17 | 0.471 | 0.328 | 0.201 |
| 16 | 0.470 | 0.329 | 0.202 |
| 15 | 0.468 | 0.330 | 0.202 |
| 14 | 0.467 | 0.331 | 0.202 |
| 13 | 0.466 | 0.333 | 0.202 |
| 12 | 0.464 | 0.334 | 0.202 |
| 11 | 0.463 | 0.335 | 0.202 |
| 10 | 0.462 | 0.336 | 0.202 |
| 9 | 0.460 | 0.337 | 0.202 |
| 8 | 0.459 | 0.339 | 0.202 |
| 7 | 0.458 | 0.340 | 0.202 |
| 6 | 0.457 | 0.341 | 0.203 |
| 5 | 0.455 | 0.342 | 0.203 |
| 4 | 0.454 | 0.343 | 0.203 |
| 3 | 0.453 | 0.345 | 0.203 |
| 2 | 0.451 | 0.346 | 0.203 |
| 1 | 0.450 | 0.347 | 0.203 |

FIG. 5

| LIGHT AMOUNT LEVEL | MIXING RATE | | |
|---|---|---|---|
| | SEMICONDUCTOR LIGHT-EMITTING DEVICE 101R | SEMICONDUCTOR LIGHT-EMITTING DEVICE 101G | SEMICONDUCTOR LIGHT-EMITTING DEVICE 101B |
| 17 (MAX) | 0.471 | 0.328 | 0.201 |
| 1 (MIN) | 0.450 | 0.347 | 0.203 |

MEDICAL LIGHT SOURCE SYSTEM, MEDICAL LIGHT SOURCE DEVICE, AND METHOD OF ADJUSTING LIGHT AMOUNT OF MEDICAL LIGHT SOURCE DEVICE

CROSS REFERENCE TO RELATED APPLICATIONS

This application is a U.S. National Phase of International Patent Application No. PCT/JP2018/005458 filed on Feb. 16, 2018, which claims priority benefit of Japanese Patent Application No. JP 2017-092847 filed in the Japan Patent Office on May 9, 2017. Each of the above-referenced applications is hereby incorporated herein by reference in its entirety.

TECHNICAL FIELD

The present disclosure relates to a medical light source system, a medical light source device, and a method of adjusting a light amount of the medical light source device.

BACKGROUND ART

When a semiconductor light-emitting device is used as a light source, a driving current is changed to change luminance of light emission. However, for the semiconductor light-emitting device, when the driving current changes, a wavelength of emitted light (spectrum) changes due to self-heating of the light source, thereby changing chromaticity (hue) of the light emitted from the light source. Particularly in a medical site where color reproducibility of appearance is strongly required, for example, it is preferable that constant chromaticity be implemented regardless of the luminance. To inhibit such a change in chromaticity, various techniques have conventionally been proposed.

One of such techniques is to inhibit wavelength fluctuation itself due to the change in the driving current by radiating a heat amount of self-heating of the semiconductor light-emitting device or cooling the semiconductor light-emitting device. In such a technique, it is important to identify a temperature of the semiconductor light-emitting device. However, in many cases, only the temperature near the semiconductor light-emitting device can be measured, and an error between a junction temperature and the temperature near the light-emitting device can occur, and therefore the measured temperature is not always accurate. Furthermore, since it is difficult to keep the junction temperature constant only by heat dissipation, it will be necessary to rely on cooling. However, due to thermal resistance between a cooling device and the junction, it is difficult to keep a constant temperature accurately. Moreover, in a case where a plurality of semiconductor light-emitting devices is used, there are various concerns such as a mounting area of the cooling device, parts costs, and an increase in power used for cooling during use.

Therefore, various methods have been proposed to keep the chromaticity constant at the time of light amount fluctuation by controlling a driving state of the semiconductor light-emitting device instead of controlling the self-heating of the semiconductor light-emitting device by cooling or other methods.

For example, Patent Document 1 below discloses a method of controlling the driving state of the semiconductor light-emitting device and keeping the chromaticity constant at the time of light amount fluctuation by analyzing a captured image captured using illumination light by predetermined arithmetic processing.

Furthermore, Patent Document 2 below discloses a method of keeping the chromaticity constant at the time of light amount fluctuation by measuring light inside a light source including a semiconductor light-emitting device and making fine adjustments to the light amount on the basis of an obtained measurement result.

CITATION LIST

Patent Document

Patent Document 1: Japanese Patent Application Laid-Open No. 2015-231553
Patent Document 2: Japanese Patent Application Laid-Open No. 2015-61569

SUMMARY OF THE INVENTION

Problems to be Solved by the Invention

However, in a case where the method disclosed in Patent Document 1 is used, in addition to a light source device, it is necessary to provide an image acquisition device or the like. Furthermore, in a case where the method disclosed in Patent Document 2 is actually used, very complicated processing is required, such as discrimination between a change in received light due to light amount fluctuation and a change in received light caused by wavelength fluctuation due to a temperature change. Thus, when the methods disclosed in Patent Document 1 and Patent Document 2 are used, a feedback system is required that identifies any state caused by light amount fluctuation and feeds back identification results to the light source device.

Consequently, in view of the above circumstances, the present disclosure proposes a medical light source system, a medical light source device, and a method of adjusting a light amount of the medical light source device that can more easily inhibit the change in chromaticity that occurs at the time of light amount fluctuation of the semiconductor light-emitting device without providing a feedback system.

Solutions to Problems

The present disclosure provides a medical light source system including: a light source unit including two or more semiconductor light-emitting devices having wavelengths of emitted light different from each other, the light source unit being configured to generate light of predetermined chromaticity by mixing the light emitted from each of the semiconductor light-emitting devices and emitting outward the generated light of the chromaticity as illumination light; and a control device configured to control a mixing rate of the light emitted from each of the semiconductor light-emitting devices in accordance with a light amount setting value of the illumination light emitted from the light source unit, the control device being configured to keep the chromaticity constant regardless of a light amount of the illumination light.

Furthermore, the present disclosure provides a medical light source device including: a light source part including two or more semiconductor light-emitting devices having wavelengths of emitted light different from each other, the light source part being configured to generate light of predetermined chromaticity by mixing the light emitted from each of the semiconductor light-emitting devices and emitting outward the generated light of the chromaticity as illumination light; and a control unit configured to control a mixing rate of the light emitted from each of the semiconductor light-emitting devices in accordance with a light amount setting value of the illumination light emitted from the light source part, the control unit being configured to keep the chromaticity constant regardless of a light amount of the illumination light.

Furthermore, the present disclosure provides a method of adjusting a light amount of a medical light source device including a light source part including two or more semiconductor light-emitting devices having wavelengths of emitted light different from each other, the light source part being configured to generate light of predetermined chromaticity by mixing the light emitted from each of the semiconductor light-emitting devices, the method including: controlling a mixing rate of the light emitted from each of the semiconductor light-emitting devices in accordance with a set light amount setting value of illumination light; and driving each of the semiconductor light-emitting devices at the mixing rate to emit the illumination light having the set light amount setting value.

The present disclosure controls the mixing rate of the light emitted from each of the semiconductor light-emitting devices in accordance with the light amount setting value of the illumination light emitted from the light source, and keeps the chromaticity constant regardless of the light amount of the illumination light.

Effects of the Invention

As described above, the present disclosure makes it possible to more easily inhibit the change in chromaticity that occurs at the time of light amount fluctuation of the semiconductor light-emitting devices without providing a feedback system.

Note that above effects are not necessarily restrictive, and in addition to or instead of the above effects, any of the effects indicated in the present specification or other effects that can be determined from the present specification may be produced.

BRIEF DESCRIPTION OF DRAWINGS

FIG. 4 is an explanatory diagram for describing the driving condition information the medical light source device according to the embodiment has.

FIG. 5 is an explanatory diagram for describing the driving condition information the medical light source device according to the embodiment has.

MODE FOR CARRYING OUT THE INVENTION

Figure 1:
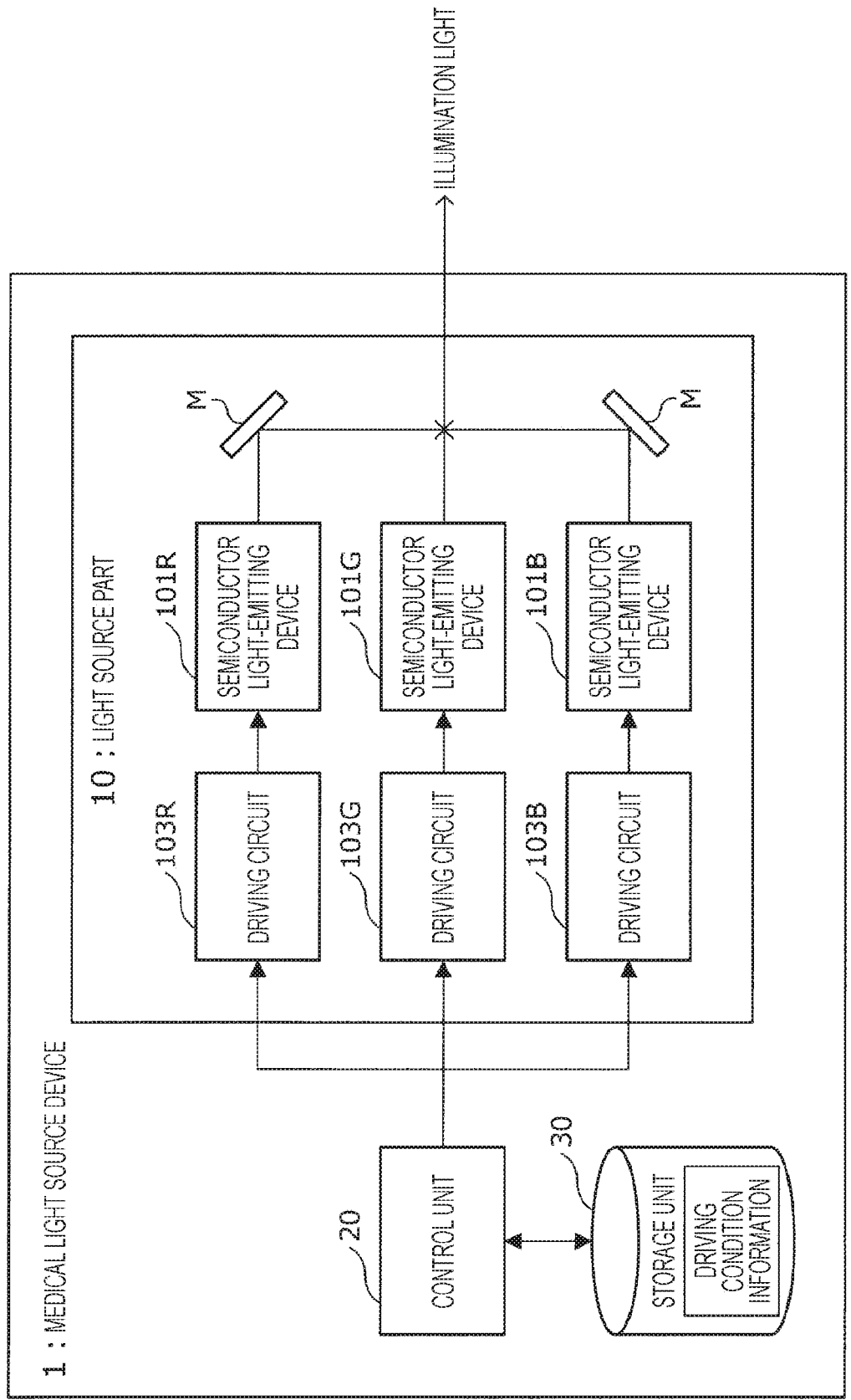
FIG. 1 is a block diagram schematically showing a configuration of a medical light source device according to an embodiment of the present disclosure.

A preferred embodiment of the present disclosure will be described in detail below with reference to the accompanying drawings. Note that in the present specification and the drawings, components having substantially the same functional configuration are denoted with the same reference symbol, and redundant description thereof will be omitted.

Note that the description will be made in the following order.
1. Embodiment
1.1. About medical light source device
About overall configuration of the medical light source device
About driving condition information
1.2. About medical light source system
About overall configuration of the medical light source system
About hardware configuration
2. Example Embodiment <About Medical Light Source Device>

A medical light source device according to an embodiment of the present disclosure will be described in detail below with reference to FIGS. 1 to 8.

The medical light source device according to the present embodiment is a light source device that can be used as an illumination light source for a medical observation system or a medical treatment system such as, for example, a medical endoscope system or a medical microscope system.

As mentioned earlier, when semiconductor light-emitting devices are used as a light source, luminance of the light is changed by changing a driving current, but in the semiconductor light-emitting devices, when the driving current changes, a wavelength (spectrum) of the light emitted due to self-heating of the light source shifts to the long wavelength side, and chromaticity (hue) of the light emitted from the light source changes. Such a wavelength change due to self-heating is about several nanometers, and the magnitude of the wavelength shift differs depending on color of the light emitted from each semiconductor light-emitting device. However, particularly in a medical site or the like where color reproducibility of appearance is strongly required, there is a possibility that, for example, the way a part of a living body to which attention is paid appears may change due to the wavelength change of about several nanometers, and there is also a possibility that a doctor or the like may make a wrong determination due to unprecedented appearance. Accordingly, the light source device used for medical treatment is required to accurately determine the chromaticity (hue) of the light to emit, and furthermore to implement constant chromaticity regardless of the light amount of the emitted light.

Consequently, the present inventors have intensively studied a light source that can more easily inhibit the change in chromaticity that occurs at the time of light amount fluctuation of the semiconductor light-emitting devices without providing various feedback systems, and as a result, the present inventors have conceived the medical light source device according to the present embodiment as detailed below.

[About Overall Configuration of the Medical Light Source Device]

The following describes in detail, as an example, a medical light source device that generates white light having a predetermined light amount by using semiconductor light-emitting devices that can emit three types of light including red light, green light, and blue light, the medical light source device emitting the generated white light outward as illumination light.

FIG. 1 is a block diagram schematically showing a configuration of a medical light source device according to the present embodiment. As shown in FIG. 1, the medical light source device 1 according to the present embodiment mainly includes a light source part 10, a control unit 20, and a storage unit 30.

The light source part 10 includes two or more semiconductor light-emitting devices 101 having wavelengths of emitted light different from each other. FIG. 1 illustrates three semiconductor light-emitting devices 101 having wavelengths of emitted light different from each other. The semiconductor light-emitting device 101R shown in FIG. 1 is a light-emitting device that emits red light, the semiconductor light-emitting device 101G is a light-emitting device that emits green light, and the semiconductor light-emitting device 101B is a light-emitting device that emits blue light. Each light emitted from each semiconductor light-emitting device 101 included in the light source part 10 is appropriately guided by known optical elements such as various mirrors M and lenses (not shown) and combined with each other, thereby generating white light. The generated white light is emitted outward from the light source part 10 and used as illumination light.

Each semiconductor light-emitting device 101 provided in the light source part 10 is provided with a driving circuit 103 for driving the semiconductor light-emitting device 101 to emit desired light. In FIG. 1, the driving circuit 103R is provided as a driving circuit for the semiconductor light-emitting device 101R, the driving circuit 103G is provided as a driving circuit for the semiconductor light-emitting device 101G, and the driving circuit 103B is provided as a driving circuit for the semiconductor light-emitting device 101B. The control unit 20 as described later appropriately drives these driving circuits 103 to apply an appropriate amount of current to each semiconductor light-emitting device 101, thereby making it possible to emit light of a desired light amount from each semiconductor light-emitting device 101.

Such semiconductor light-emitting devices 101 and driving circuits 103 are not particularly limited, and various known semiconductor light-emitting devices 101 and driving circuits 103 can be used in combination as appropriate in accordance with chromaticity of the light emitted from the medical light source device 1.

The control unit 20 is implemented by, for example, a central processing unit (CPU), a read only memory (ROM), a random access memory (RAM), a communication device, or the like. The control unit 20 controls a mixing rate of the light emitted from each semiconductor light-emitting device 101 in accordance with a light amount setting value of the illumination light emitted from the light source part 10, and keeps the chromaticity of the illumination light constant regardless of the light amount of the illumination light.

In more detail, if a user of the medical light source device 1 according to the present embodiment (for example, a doctor or the like) sets the light amount of the illumination light to be emitted from the medical light source device 1, the control unit 20 determines the mixing rate of the light emitted from each semiconductor light-emitting device 101 in accordance with the light amount setting value. Thereafter, the control unit 20 outputs a predetermined control signal to each driving circuit 103 such that a current value for implementing the determined mixing rate is applied to each semiconductor light-emitting device 101.

Here, when determining the mixing rate of the light emitted from each semiconductor light-emitting device 101, the control unit 20 uses information indicating a driving condition of the semiconductor light-emitting device 101, the information being stored in the storage unit 30 as described later (hereinafter referred to as "driving condition information"). Such driving condition information will be described again in more detail below.

The control unit 20 outputs the predetermined control signal to the driving circuit 103, whereby the predetermined current value is applied to each semiconductor light-emitting device 101, and light having a predetermined wavelength (in a case where the current value causes a wavelength shift, the light has a wavelength after the wavelength shift has occurred) is emitted from each semiconductor light-emitting device 101. As described later, in the driving condition information used by the control unit 20, the mixing rate of the light emitted from each semiconductor light-emitting device 101 is defined in consideration of the wavelength shift that occurs in each semiconductor light-emitting device 101. Therefore, the medical light source device 1 according to the present embodiment can keep chromaticity constant regardless of the light amount of the illumination light.

Furthermore, the control unit 20 can control the combination of the light emitted from each semiconductor light-emitting device 101 by performing on/off control of the semiconductor light-emitting devices 101 of the light source part 10. This allows the medical light source device 1 according to the present embodiment to generate illumination light having various chromaticity other than white light by changing the combination of the light emitted from the semiconductor light-emitting devices 101.

The storage unit 30 is implemented by, for example, a RAM, a storage device, or the like included in the medical light source device 1 according to the present embodiment. In the storage unit 30, the driving condition information as previously mentioned briefly has been stored in advance. Furthermore, in addition to such driving condition information, various parameters, processing in progress, and the like the medical light source device 1 (especially, control unit 20) according to the present embodiment needs to save when performing some processing, or various databases, programs, and the like are appropriately recorded in the storage unit 30. The storage unit 30 allows the light source part 10 and the control unit 20 to freely perform read/write processing of data.

The overall configuration of the medical light source device 1 according to the present embodiment has been described in detail above with reference to FIG. 1.

[About Driving Condition Information]

Next, with reference to FIGS. 2 to 8, the driving condition information to be referred to when the control unit 20 performs adjustment processing on illumination light chromaticity in accordance with the light amount setting value will be described in detail.

Figure 6:
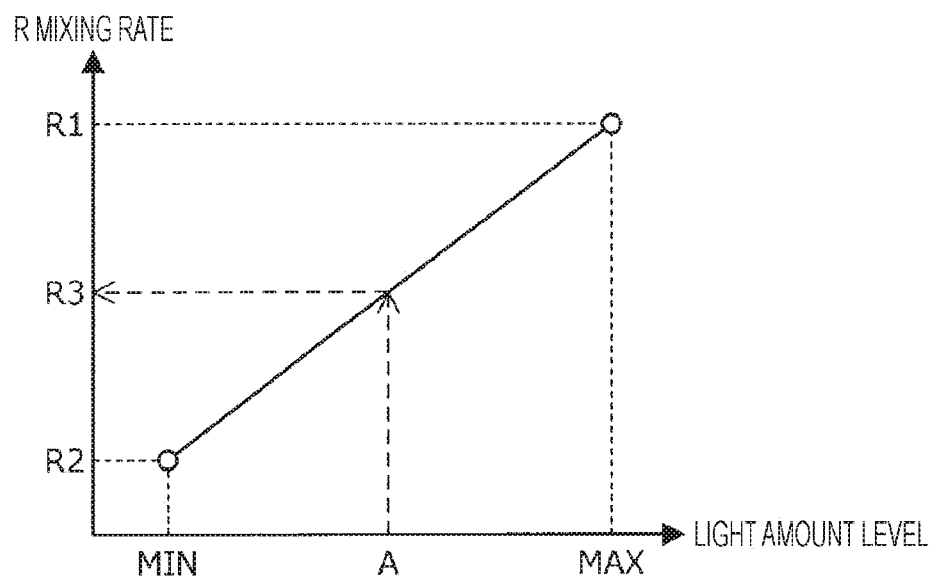
FIG. 6 is an explanatory diagram for describing the driving condition information the medical light source device according to the embodiment has.
Figure 7:
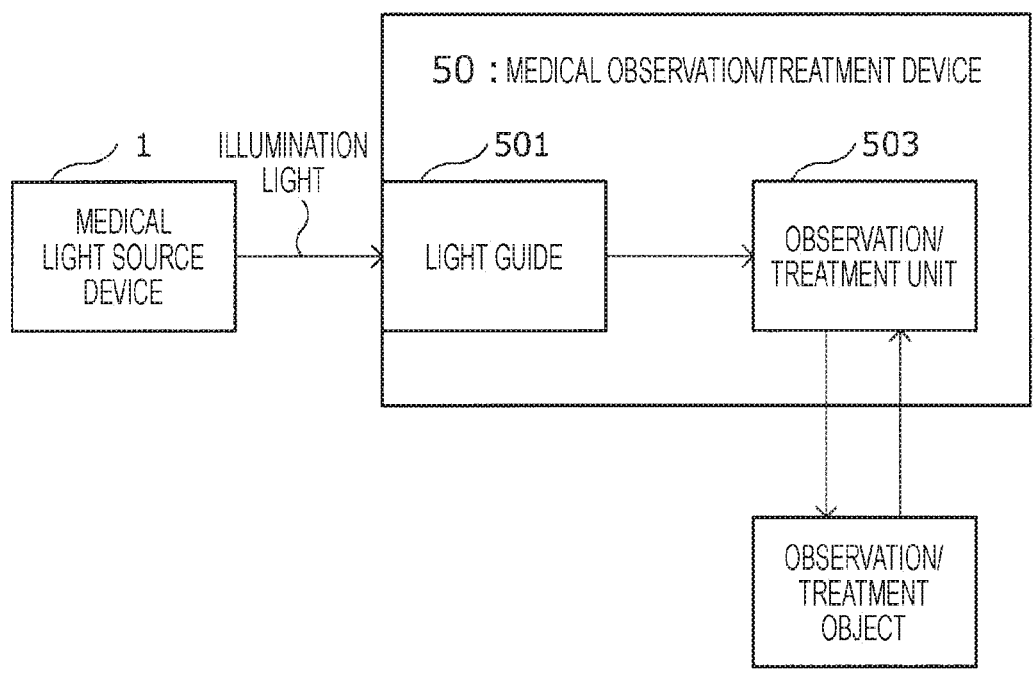
FIG. 7 is an explanatory diagram for describing a configuration of a medical observation/treatment device.

FIGS. 2 to 6 and 8 are explanatory diagrams for describing the driving condition information the medical light source device according to the present embodiment has. FIG. 7 is an explanatory diagram for describing a configuration of a medical observation/treatment device.

In the medical light source device 1 according to the present embodiment as shown in FIG. 1, if a light amount level of illumination light (light amount setting value) is set by a user such as a doctor, the control unit 20 sets optimal light combination (mixing rate) at the light amount level set on the basis of the driving condition information. The driving condition information that is referred to when the mixing rate is set is information indicating the driving condition of the semiconductor light-emitting devices 101 in which the light amount setting value that is set for the light source part 10 is associated with the mixing rate of the light emitted from each semiconductor light-emitting device 101. In this driving condition information, for example, as schematically shown in FIG. 2, in the medical light source device 1 according to the present embodiment, in a case where it is possible to set n-tier light amount levels (light amount setting values, FIG. 2 shows a 20-tier case), the mixing ratio of each semiconductor light-emitting device 101 is set such that chromaticity (hue) of the illumination light becomes constant at each light amount level.

Figures 2, 3:
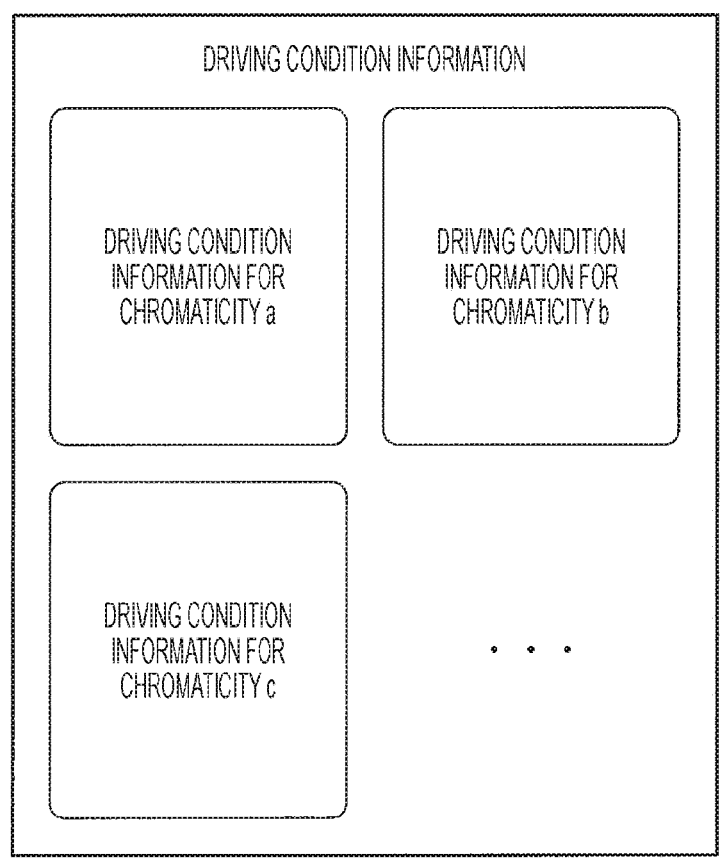
FIG. 2 is an explanatory diagram for describing driving condition information the medical light source device according to the embodiment has.
FIG. 3 is an explanatory diagram for describing the driving condition information the medical light source device according to the embodiment has.

The mixing rate of the light emitted from each semiconductor light-emitting device as shown in FIG. 2 can be identified in advance by performing known simulation or the like, and such a method of identifying the mixing rate is not particularly limited.

Furthermore, for example, as schematically shown in FIG. 3, it is preferable to provide the driving condition information as shown in FIG. 2 for each chromaticity of the illumination light that can be generated by the medical light source device 1. For example, in a case where the medical light source device 1 as shown in FIG. 1 can select chromaticity of illumination light from among m types, the storage unit 30 preferably stores m pieces of driving condition information for each chromaticity of illumination light.

Example of Driving Condition Information-1

In the driving condition information shown in FIG. 4, in a case where the 17-tier light amount levels (light amount setting values) can be set, the mixing ratio of each semiconductor light-emitting device 101 is associated with each light amount level, in the medical light source device 1 according to the present embodiment. Here, in the example shown in FIG. 4, the light amount level=17 corresponds to the maximum light amount in the medical light source device 1, and the light amount level=1 corresponds to the minimum light amount in the medical light source device 1.

As illustrated in FIG. 4, in the driving condition information according to the present embodiment, the mixing rates of the light emitted from the semiconductor light-emitting devices 101 is associated with each set light amount level. The mixing rate described in the driving condition information is determined in advance such that chromaticity of illumination light is constant between light amount levels in consideration of the wavelength shift that occurs in each semiconductor light-emitting device 101. Accordingly, the control unit 20 can identify the driving state of the semiconductor light-emitting devices 101 for implementing the mixing rates described in the driving condition information with reference to the driving condition information as shown in FIG. 4 stored in the storage unit 30 on the basis of the set light amount setting values.

The control unit 20 identifies the magnitude of the current value to be applied to each semiconductor light-emitting device 101 by a known method in order to implement the mixing rates described in the driving condition information, and outputs the control signal for causing the driving circuit 103 to apply the identified current value to the semiconductor light-emitting device 101. This makes it possible to cause each semiconductor light-emitting device 101 to illuminate at the mixing rate for implementing the desired chromaticity of the illumination light. As a result, by using a simple method of referring to the driving condition information, it is possible to inhibit the change in chromaticity that occurs at the time of light amount fluctuation of the semiconductor light-emitting devices without providing a feedback system, and to keep the chromaticity of the illumination light constant regardless of the light amount of the illumination light.

Example of Driving Condition Information-2

In the configuration of the driving condition information as illustrated in FIG. 4, n R/G/B mixing rates are set for the n-tier light amounts. Therefore, it takes time to input in advance the mixing rates at each light amount level. Also, as the number of tiers of the light amount n increases, the data size of the driving condition information also increases, and it is required to secure adequate capacity of the storage unit 30. Furthermore, in the driving condition information as illustrated in FIG. 4, it is difficult to flexibly change the light amount because only a fixed n-tier combination of mixing rates can be implemented.

Consequently, as illustrated in FIG. 5, as the driving condition information, only the maximum light amount setting value and the minimum light amount setting value that are set for the light source part 10 may be associated with the mixing rates of the light emitted from each semiconductor light-emitting device 101.

For such driving condition information, if the light amount setting value set for the light source part 10 is the maximum light amount setting value or the minimum light amount setting value, on the basis of the set light amount setting value, the control unit 20 controls the driving state of each semiconductor light-emitting device 101 in a similar manner to described above with reference to the driving condition information stored in the storage unit 30.

Furthermore, if the set light amount setting value is neither the maximum light amount setting value nor the minimum light amount setting value, on the basis of the driving condition information stored in the storage unit 30, the control unit 20 calculates the mixing rates of the light emitted from the semiconductor light-emitting devices 101 at the set light amount setting value. The mixing rates of light at light amount setting values positioned between the maximum light amount setting value and the minimum light amount setting value are calculated by various known interpolation methods on the basis of the set light amount setting values. Such an interpolation method may be a linear interpolation method as illustrated in FIG. 6, a second-order or higher interpolation method may be used, or a non-linear interpolation method may be used. Such an interpolation method is only required to be appropriately selected in accordance with light emission characteristics of the semiconductor light-emitting devices 101 to use.

FIG. 6 illustrates a method of calculating the mixing rate in the semiconductor light-emitting device 101R by linear interpolation. In the driving condition information as shown in FIG. 5, an R mixing rate R1 at the maximum light amount setting value (MAX) of the semiconductor light-emitting device 101R and an R mixing rate R2 at the minimum light amount setting value (MIN) of the semiconductor light-emitting device 101R are described. Consequently, the control unit 20 can calculate an R mixing rate R3 at any light amount setting value A positioned between MIN and MAX from the set light amount setting value A and an equation of the straight line shown in FIG. 6. The mixing rates at the set light amount setting value A can be calculated by performing similar processing on the semiconductor light-emitting devices 101G and 101B.

Thereafter, the control unit 20 identifies, by a known method, the magnitude of the current value to be applied to each semiconductor light-emitting device 101 in order to implement the mixing rate calculated as described above, and outputs the control signal for causing the driving circuit 103 to apply the identified current value to the semiconductor light-emitting device 101. Thus, for any light amount setting value, each semiconductor light-emitting device 101 can be illuminated at the mixing rate for implementing the desired chromaticity of the illumination light.

About Specific Values of Mixing Rate

Note that fine adjustments may be made to the specific mixing rate values as shown in FIGS. 4 and 5 by a producer when the medical light source device 1 is shipped. With the adjustments, even if there is an individual difference in the light emission characteristics of each semiconductor light-emitting device 101, it is possible to more reliably inhibit the change in chromaticity that occurs at the time of light amount fluctuation of the semiconductor light-emitting device. Furthermore, fine adjustments may be made to the specific mixing rate values as shown in FIGS. 4 and 5 by a user of the medical light source device 1 at any timing. With the adjustments, even if the light emission characteristics of the semiconductor light-emitting device 101 change over time, it is possible to more reliably inhibit the change in chromaticity that occurs at the time of light amount fluctuation of the semiconductor light-emitting device.

By using the driving condition information as described above, the medical light source device 1 according to the present embodiment can inhibit the magnitude of chromaticity variation of illumination light between the light amount levels up to the color temperature of about 100 K. If it is considered that the chromaticity variation in the color temperature of about several hundred K to 1000 K occurs depending on the light amount level in a case where the above wavelength shift is not taken into consideration, it can be understood that the change in chromaticity of the illumination light can be effectively inhibited by using the driving condition information as described above.

Modification of Driving Condition Information 1

As a further advantage of the two types of driving condition information as described above, the mixing rate can be set at each of the minimum light amount setting value and the maximum light amount setting value. In order to obtain chromaticity of illumination light, methods such as calculating the mixing rate by known simulation can be used, and an amount of spectral change accompanying the temperature fluctuation due to self-heating is about several nanometers. Meanwhile, at the present time, the minimum resolution of a measuring instrument for measuring the amount of spectral change accompanying the wavelength shift has become excellent resolution, for example, 1 nm or the like. While it is possible to make more accurate measurements by using such a high resolution measuring instrument and improve the accuracy of the mixing rate, in a case where a plurality of mixing rates can be set as in the present embodiment, it is also possible to set the mixing rates so as to minimize fluctuation among all light amount setting values. This makes it possible to stabilize the chromaticity (hue) when changing the light amount more than the wavelength resolution of the measuring instrument or the simulation accuracy.

Modification of Driving Condition Information 2

Furthermore, for example, as schematically shown in FIG. 7, consider a case where the medical light source device 1 according to the present embodiment is used as an external light source for various medical observation/treatment devices 50 such as a medical microscope or a medical endoscope. In this case, illumination light having chromaticity that is kept constant and emitted from the medical light source device 1 is guided to the inside of the medical observation/treatment device 50 by optical connection to a light guide 501, which is a light guiding optical device provided in the medical observation/treatment device 50. The illumination light connected to the light guide 501 is appropriately guided by an observation/treatment unit 503 represented by, for example, a microscope unit, an endoscope unit, or the like, and is emitted onto an observation/treatment object.

Figure 8:
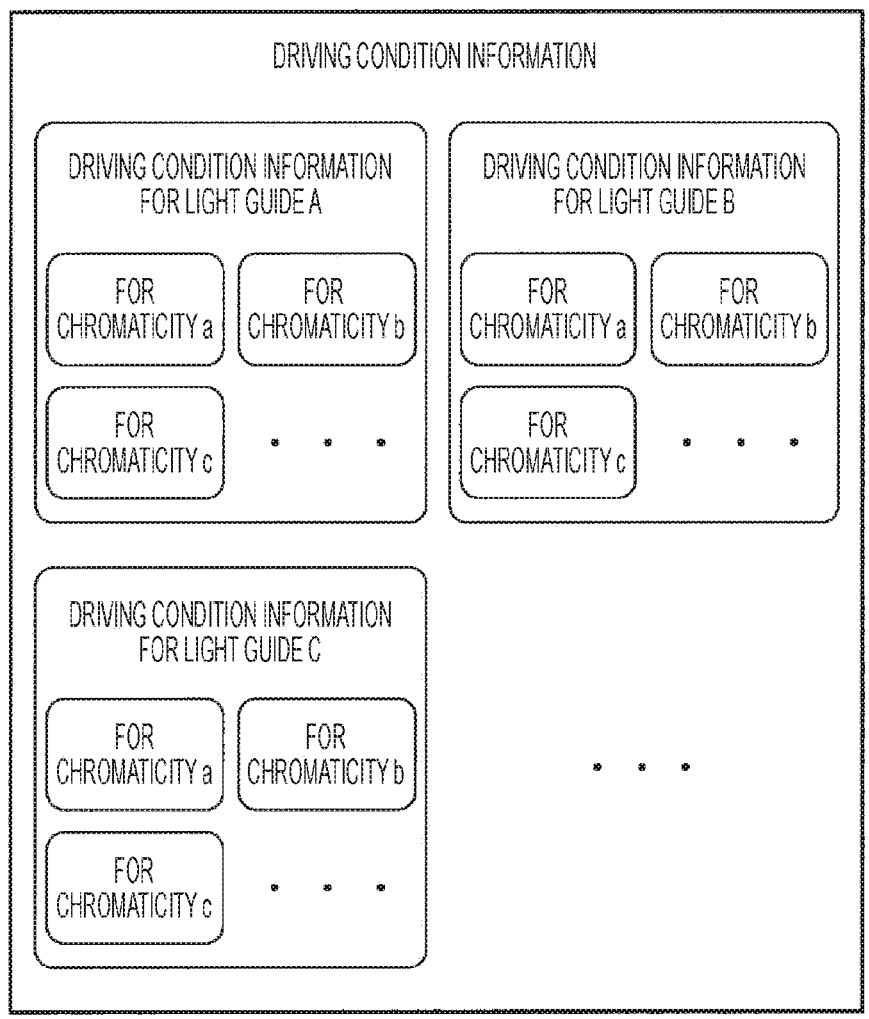
FIG. 8 is an explanatory diagram for describing the driving condition information the medical light source device according to the embodiment has.

Here, in order to more reliably keep chromaticity of the illumination light constant, determination may be made on the basis of not only optical characteristics of the semiconductor light-emitting device 101 provided in the medical light source device 1, but also optical characteristics of the light guide 501, which is a light guiding optical device. In that case, as schematically shown in FIG. 8, a plurality of pieces of driving condition information may be stored in the storage unit 30 for each type of the light guide 501. This makes it possible to properly select the driving condition information optimum for the light guide 501 mounted in the medical observation/treatment device 50, and to more reliably keep the chromaticity of the illumination light constant.

The driving condition information according to the present embodiment has been described in detail above with reference to FIGS. 2 to 8.

One example of functions of the medical light source device 1 according to the present embodiment has been described above. Functions of the control unit 20 and the storage unit 30 described above may include general-purpose members or circuits, or may include hardware specialized for the functions of respective components. Furthermore, all the functions of the control unit 20 and the storage unit 30 as described above may be performed by a CPU or the like. Accordingly, it is possible to change the configuration to use as appropriate in accordance with the technical level when the present embodiment is implemented.

<About Medical Light Source System>

Next, a medical light source system 3 according to the present embodiment will be briefly described with reference to FIGS. 9 and 10.

Figure 9:
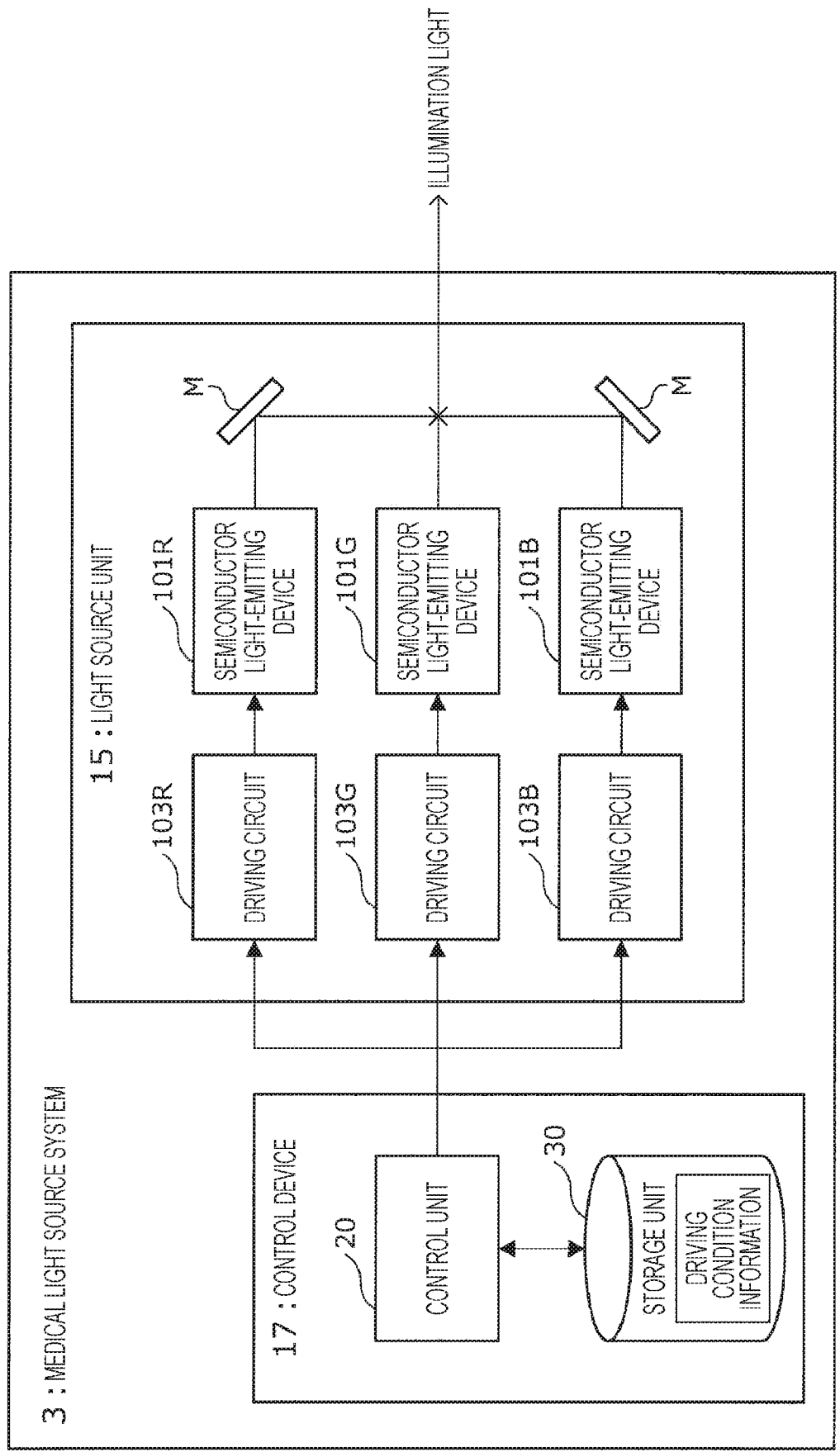
FIG. 9 is a block diagram schematically showing a configuration of a medical light source system according to the embodiment.
Figure 10:
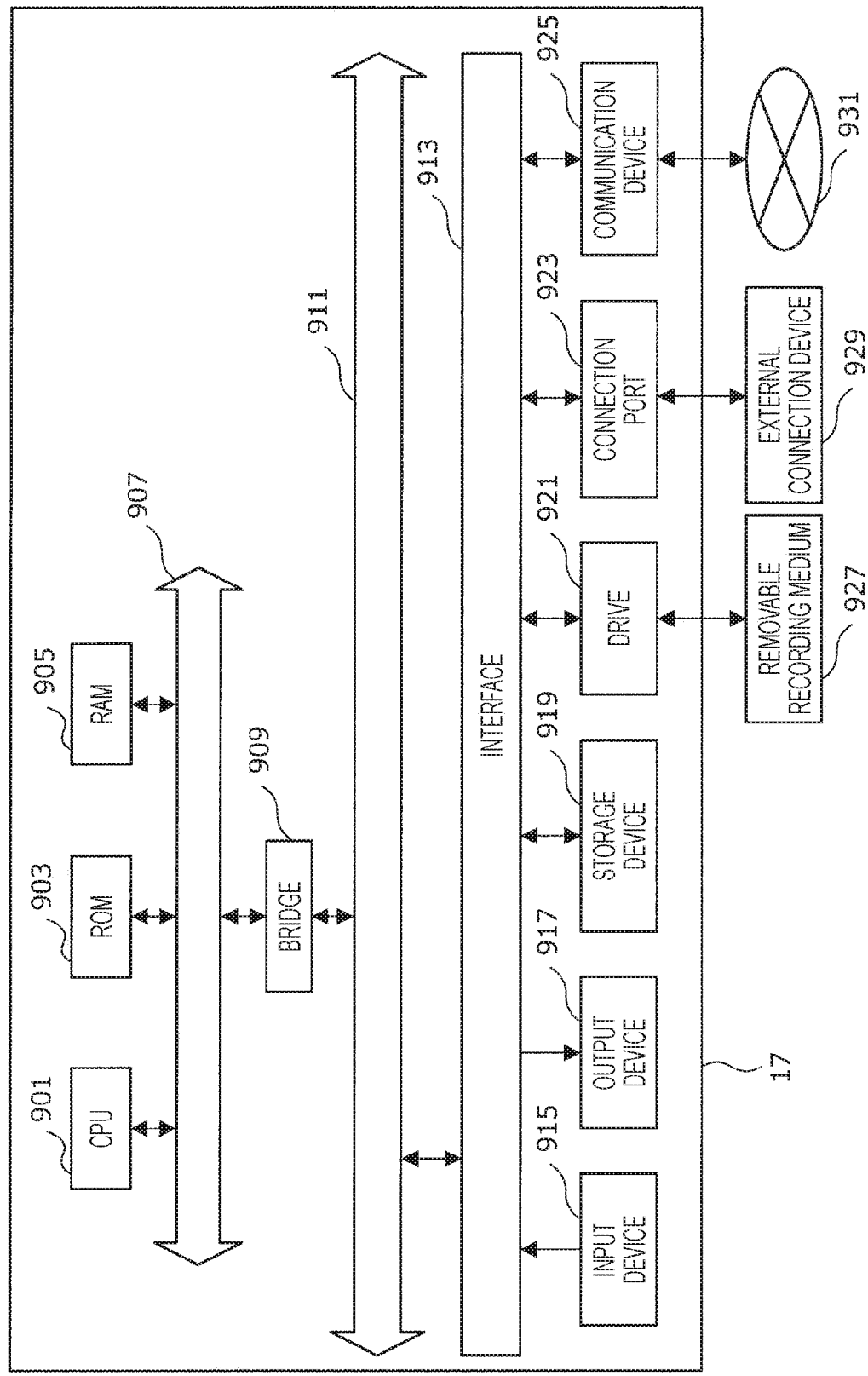
FIG. 10 is a block diagram schematically showing one example of a hardware configuration of a control device of the medical light source system according to the embodiment.

FIG. 9 is a block diagram schematically showing a configuration of the medical light source system according to the present embodiment, and FIG. 10 is a block diagram schematically showing one example of the hardware configuration of the control device of the medical light source system according to the present embodiment.

[About Overall Configuration of the Medical Light Source System]

The medical light source device 1 according to the present embodiment described earlier has been an integration of the light source part 10, the control unit 20, and the storage unit 30. Meanwhile, the above effects may be produced with a configuration in which the light source part 10, the control unit 20, and the storage unit 30 are separate devices, and these devices function in cooperation with one another as a system.

Such a medical light source system 3 includes a light source unit 15 and a control device 17 as schematically shown in FIG. 9.

Here, the light source unit 15 has a configuration similar to the configuration of the light source part 10 shown in FIG. 1, and includes a plurality of semiconductor light-emitting devices 101 and a plurality of driving circuits 103 that drives the semiconductor light-emitting devices 101. The semiconductor light-emitting devices 101 and the driving circuits 103 constituting the light source unit 15 have functions similar to the functions of the semiconductor light-emitting devices 101 and the driving circuits 103 in the medical light source device 1 shown in FIG. 1, and produce similar effects. Therefore, detailed descriptions will be omitted below.

Furthermore, the control device 17 is a device that implements the functions of the control unit 20 and the storage unit 30 shown in FIG. 1, and includes the control unit 20 and the storage unit 30. The control unit 20 and the storage unit 30 included in the control device 17 have functions similar to the functions of the control unit 20 and the storage unit 30 in the medical light source device 1 shown in FIG. 1, and produce similar effects. Therefore, detailed descriptions will be omitted below.

Here, the light source unit 15 constituting the medical light source system 3 according to the present embodiment may be an existing light source unit including a plurality of semiconductor light-emitting devices. Connection of the control device 17 according to the present embodiment to the existing light source unit makes it possible to inhibit the chromaticity change that occurs at the time of light amount fluctuation of the semiconductor light-emitting devices as described above.

[About Hardware Configuration]

Next, a hardware configuration of the control device 17 according to the present embodiment will be described in detail with reference to FIG. 10. FIG. 10 is a block diagram for describing the hardware configuration of the control device 17 according to the embodiment of the present disclosure.

The control device 17 mainly includes a CPU 901, a ROM 903, and a RAM 905. Furthermore, the control device 17 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls the entire operation or part of the operation in the control device 17 in accordance with various programs recorded in the ROM 903, the RAM 905, the storage device 919, or a removable recording medium 927. The ROM 903 stores programs, calculation parameters, and the like to be used by the CPU 901. The RAM 905 primarily stores the programs to be used by the CPU 901, parameters that appropriately change in the execution of the programs, and the like. These are mutually connected by the host bus 907 including an internal bus such as a CPU bus.

The host bus 907 is connected to the external bus 911 such as a peripheral component interconnect/interface (PCI) bus via the bridge 909.

The input device 915 is, for example, an operation unit operated by a user, such as a mouse, a keyboard, a touch panel, a button, a switch, or a lever. Furthermore, the input device 915 may be, for example, a remote control unit (so-called remote control) using infrared rays or other radio waves, or an external connection device 929 that supports the operation of the control device 17 such as a mobile phone or a PDA. Moreover, the input device 915 includes, for example, an input control circuit or the like that generates an input signal on the basis of information input by a user by using the above-described operation unit and outputs the generated signal to the CPU 901. By operating the input device 915, the user of the control device 17 can input various data into the control device 17 and instruct processing operations.

The output device 917 includes a device that can visually or aurally notify the user of acquired information. Examples of such a device include a display device such as a CRT display device, a liquid crystal display device, a plasma display device, an EL display device, and a lamp, a voice output device such as a speaker or a headphone, a printer device, a mobile phone, a facsimile, and the like. The output device 917 outputs, for example, a result obtained by various types of processing performed by the control device 17. Specifically, the display device displays the result obtained by the various types of processing performed by the control device 17 as text or images. Meanwhile, the voice output device converts an audio signal including reproduced voice data, acoustic data, and the like into an analog signal and outputs the analog signal.

The storage device 919 is a device for data storage as one example of a storage unit of the control device 17. The storage device 919 includes, for example, a magnetic storage device such as a hard disk drive (HDD), a semiconductor storage device, an optical storage device, or a magneto-optical storage device, and the like. The storage device 919 stores programs to be executed by the CPU 901, various data, externally acquired various data, and the like.

The drive 921 is a reader/writer for a recording medium, and is built in or externally attached to the control device 17. The drive 921 reads information recorded in the mounted removable recording medium 927 such as a magnetic disk, an optical disk, a magneto-optical disk, or a semiconductor memory, and outputs the information to the RAM 905. Furthermore, the drive 921 can also write a record on the mounted removable recording medium 927 such as a magnetic disk, an optical disk, a magneto-optical disk, or a semiconductor memory. The removable recording medium 927 is, for example, a DVD medium, an HD-DVD medium, a Blu-ray (registered trademark) medium, or the like. Furthermore, the removable recording medium 927 may be a compact flash (CF) (registered trademark), a flash memory, a secure digital (SD) memory card, or the like. Furthermore, the removable recording medium 927 may be, for example, an integrated circuit (IC) card or an electronic device on which a non-contact IC chip is mounted, or the like.

The connection port 923 is a port for directly connecting a device to the control device 17. One example of the connection port 923 includes a universal serial bus (USB) port, an IEEE 1394 port, and a small computer system interface (SCSI) port, and the like. Another example of the connection port 923 includes an RS-232C port, an optical audio terminal, a high-definition multimedia interface (HDMI) (registered trademark) port, and the like. By connecting the external connection device 929 to the connection port 923, the control device 17 acquires various data directly from the external connection device 929 or provides various data to the external connection device 929.

The communication device 925 is, for example, a communication interface including a communication device or the like for connecting to the communication network 931. The communication device 925 is, for example, a communication card for a wired or wireless local area network (LAN), Bluetooth (registered trademark), wireless USB (WUSB), or the like. Furthermore, the communication device 925 may be a router for optical communication, a router for asymmetric digital subscriber line (ADSL), a modem for various communications, or the like. The communication device 925 can, for example, transmit and receive signals or the like to and from the Internet or other communication devices in accordance with a predetermined protocol such as TCP/IP, for example. Furthermore, the communication network 931 connected to the communication device 925 includes a network or the like connected by wire or wirelessly, and may be, for example, the Internet, a home LAN, infrared communication, radio wave communication, satellite communication, or the like.

One example of the hardware configuration that can implement the function of the control device 17 according to the embodiment of the present disclosure has been described above. Each component described above may use a general-purpose member or may include hardware specialized for the function of each component. Accordingly, it is possible to change the hardware configuration to use as appropriate depending on the technical level when the present embodiment is implemented.

Example

The following specifically describes the medical light source device 1 according to the embodiment of the present disclosure with reference to an example. Note that the example shown below is just one example of the medical light source device 1 according to the embodiment of the present disclosure, and the medical light source device according to the present disclosure is not limited to the following example.

In the following example, a semiconductor laser device capable of emitting red light with a wavelength of 638 nm was used as the semiconductor light-emitting device 101R, a semiconductor laser device capable of emitting green light with a wavelength of 525 nm was used as the semiconductor light-emitting device 101G, and a semiconductor laser device capable of emitting blue light with a wavelength of 445 nm was used as the semiconductor light-emitting device 101B.

Known simulation was performed in advance to create the driving condition information shown in FIG. 5. The light amount level is set at 17 tiers, and the mixing rates other than at the minimum light amount level and the maximum light amount level were calculated by linear interpolation by equally dividing a difference between the minimum light amount level and the maximum light amount level.

Figure 11:
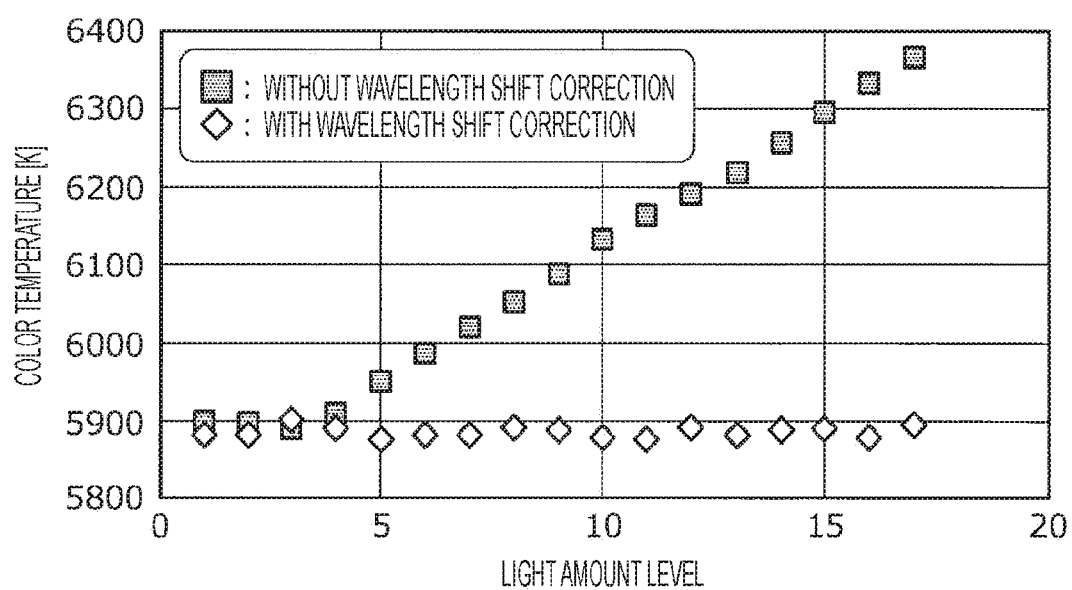
FIG. 11 is a graph showing a result obtained in an example.

For each light amount level, the color temperature of the illumination light actually emitted from the light source part is measured by using the mixing rates identified as described above (in other words, wavelength shift correction is performed), and is shown in FIG. 11. In FIG. 11, the horizontal axis is the light amount level, and the vertical axis is the color temperature [K] obtained as a result of the measurement.

Furthermore, for comparison, as a case where the mixing rates as described above are not used (in other words, as a case where the wavelength shift correction is not performed), the color temperature in a case where the semiconductor laser device is driven at each light amount level as usual is measured together, and an obtained result is shown together in FIG. 11.

As is obvious from FIG. 11, by using the driving condition information according to the embodiment of the present disclosure and controlling the driving state of each semiconductor laser device, the color temperature of the illumination light can be kept at approximately 5900 K regardless of the light amount level. From such results, it has become obvious that it is possible to inhibit the chromaticity change that occurs at the time of light amount fluctuation of the semiconductor light-emitting device by using the driving condition information according to the embodiment of the present disclosure and controlling the driving state of each semiconductor laser device.

Meanwhile, it is understood that in a case where the above mixing rates are not used, as the light amount level increases, the color temperature of the illumination light also rises, and the difference in the color temperature of the illumination light becomes about 500 K at maximum.

The preferred embodiment of the present disclosure has been described in detail above with reference to the accompanying drawings, but the technical scope of the present disclosure is not limited to such an example. It is obvious that persons of ordinary skill in the technical field of the present disclosure can conceive various modifications or alterations within the scope of the technical idea described in the claims, and it is of course understood that these also fall within the technical scope of the present disclosure.

Furthermore, the effects described in the present specification are merely descriptive or illustrative and not restrictive. That is, the technique according to the present disclosure can produce other effects obvious to those skilled in the art from the description in the present specification, in addition to or instead of the effects described above.

Note that the following configurations also belong to the technical scope of the present disclosure.

(1)

A medical light source system including:

a light source unit including two or more semiconductor light-emitting devices having wavelengths of emitted light different from each other, the light source unit being configured to generate light of predetermined chromaticity by mixing the light emitted from each of the semiconductor light-emitting devices and emitting outward the generated light of the chromaticity as illumination light; and a control device configured to control a mixing rate of the light emitted from each of the semiconductor light-emitting devices in accordance with a light amount setting value of the illumination light emitted from the light source unit, the control device being configured to keep the chromaticity constant regardless of a light amount of the illumination light.

(2)

A medical light source device including:

a light source part including two or more semiconductor light-emitting devices having wavelengths of emitted light different from each other, the light source part being configured to generate light of predetermined chromaticity by mixing the light emitted from each of the semiconductor light-emitting devices and emitting outward the generated light of the chromaticity as illumination light; and a control unit configured to control a mixing rate of the light emitted from each of the semiconductor light-emitting devices in accordance with a light amount setting value of the illumination light emitted from the light source part, the control unit being configured to keep the chromaticity constant regardless of a light amount of the illumination light.

(3)

The medical light source device according to (2), in which the control unit implements a desired mixing rate by controlling a current amount applied to each of the semiconductor light-emitting devices.

(4)

The medical light source device according to (2) or (3), further including a storage unit configured to store information indicating a driving condition of each of the semiconductor light-emitting devices in which the light amount setting value set for the light source part is associated with the mixing rate of the light emitted from each of the semiconductor light-emitting devices, in which the control unit controls a driving state of each of the semiconductor light-emitting devices on the basis of the set light amount setting value with reference to the information indicating the driving condition stored in the storage unit.

(5)

The medical light source device according to (2) or (3), further including a storage unit configured to store information indicating a driving condition of each of the semiconductor light-emitting devices in which each of a maximum light amount setting value and a minimum light amount setting value set for the light source part is associated with the mixing rate of the light emitted from each of the semiconductor light-emitting devices, in which in a case where the set light amount setting value is the maximum light amount setting value or the minimum light amount setting value, the control unit controls a driving state of each of the semiconductor light-emitting devices on the basis of the set light amount setting value with reference to the information indicating the driving condition stored in the storage unit, and in a case where the set light amount setting value is neither the maximum light amount setting value nor the minimum light amount setting value, the control unit calculates the mixing rate of the light emitted from each of the semiconductor light-emitting devices at the set light amount setting value on the basis of the information indicating the driving condition stored in the storage unit, the control unit controlling the driving state of each of the semiconductor light-emitting devices in accordance with the calculated mixing rate.

(6)

The medical light source device according to (4), in which the information indicating the driving condition of each of the semiconductor light-emitting devices is provided for each of the chromaticity of the illumination light.

(7)

The medical light source device according to (5), in which the information indicating the driving condition of each of the semiconductor light-emitting devices is provided for each of the chromaticity of the illumination light.

(8)

The medical light source device according to (4), in which the information indicating the driving condition of each of the semiconductor light-emitting devices is provided for each type of a light guiding optical device to which the illumination light is optically connected.

(9)

The medical light source device according to (5), in which the information indicating the driving condition of each of the semiconductor light-emitting devices is provided for each type of a light guiding optical device to which the illumination light is optically connected.

(10)

A method of adjusting a light amount of a medical light source device including a light source part including two or more semiconductor light-emitting devices having wavelengths of emitted light different from each other, the light source part being configured to generate light of predetermined chromaticity by mixing the light emitted from each of the semiconductor light-emitting devices, the method including:

controlling a mixing rate of the light emitted from each of the semiconductor light-emitting devices in accordance with a set light amount setting value of illumination light; and driving each of the semiconductor light-emitting devices at the mixing rate to emit the illumination light having the set light amount setting value.

REFERENCE SIGNS LIST

1 Medical light source device
3 Medical light source system
10 Light source part
15 Light source unit
17 Control device
20 Control unit
30 Storage unit
101 Semiconductor light-emitting device
103 Driving circuit

The invention claimed is:

1. A medical light source system, comprising:
a light source unit including at least two semiconductor light-emitting devices, wherein
each of the at least two semiconductor light-emitting devices is configured to emit light,
the light emitted by a first semiconductor light-emitting device of the at least two semiconductor light-emitting devices has a wavelength different from the light emitted by a second semiconductor light-emitting device of the at least two semiconductor light-emitting devices, and
the light source unit is configured to:
generate light of specific chromaticity based on mixture of the light emitted from each of the at least two semiconductor light-emitting devices; and
emit outward the generated light of the specific chromaticity as illumination light; and
a control device configured to:
determine a mixing rate of the light emitted from each of the at least two semiconductor light-emitting devices, wherein
the determination of the mixing rate is based on a light amount setting value of the illumination light emitted from the light source unit, and
the light amount setting value is based on a user operation; and
control, based on the determined mixing rate, a driving state of each of the at least two semiconductor light-emitting devices such that the specific chromaticity is constant regardless of a light amount of the illumination light.

2. A medical light source device, comprising:
a light source part including at least two semiconductor light-emitting devices, wherein
each of the at least two semiconductor light-emitting devices is configured to emit light, the light emitted by a first semiconductor light-emitting device of the at least two semiconductor light-emitting devices has a wavelength different from the light emitted by a second semiconductor light-emitting device of the at least two semiconductor light-emitting devices, and the light source part is configured to:
  generate light of specific chromaticity based on mixture of the light emitted from each of the at least two semiconductor light-emitting devices; and
  emit outward the generated light of the specific chromaticity as illumination light; and a control unit configured to:
  determine a mixing rate of the light emitted from each of the at least two semiconductor light-emitting devices, wherein
    the determination of the mixing rate is based on a light amount setting value of the illumination light emitted from the light source part, and
    the light amount setting value is based on a user operation; and
  control, based on the determined mixing rate, a driving state of each of the at least two semiconductor light-emitting devices such that the specific chromaticity is constant regardless of a light amount of the illumination light.

3. The medical light source device according to claim 2, wherein the control unit is further configured to implement the determined mixing rate by control of a current amount applied to each of the at least two semiconductor light-emitting devices.

4. The medical light source device according to claim 2, further comprising a storage unit configured to store condition information indicating a driving condition of each of the at least two semiconductor light-emitting devices, wherein
  the condition information includes the light amount setting value for the light source part in association with the mixing rate of the light emitted from each of the at least two semiconductor light-emitting devices, and
  the control unit is further configured to control the driving state of each of the at least two semiconductor light-emitting devices based on the light amount setting value and the condition information indicating the driving condition stored in the storage unit.

5. The medical light source device according to claim 4, wherein the storage unit is further configured to store the condition information for each chromaticity of the illumination light.

6. The medical light source device according to claim 4, wherein
  the illumination light is optically connected to a light guiding optical device, and
  the storage unit is further configured to store the condition information for each type of a plurality of types of the light guiding optical device.

7. The medical light source device according to claim 2, further comprising a storage unit configured to store condition information indicating a driving condition of each of the at least two semiconductor light-emitting devices, wherein
  the condition information includes a maximum light amount setting value and a minimum light amount setting value for the light source part in association with the mixing rate of the light emitted from each of the at least two semiconductor light-emitting devices,
  in a case where the light amount setting value is one of the maximum light amount setting value or the minimum light amount setting value, the control unit is further configured to control the driving state of each of the at least two semiconductor light-emitting devices based on the light amount setting value and the condition information indicating the driving condition stored in the storage unit,
  in a case where the light amount setting value is different from each of the maximum light amount setting value and the minimum light amount setting value, the control unit is further configured to calculate the mixing rate of the light emitted from each of the at least two semiconductor light-emitting devices,
  the calculation of the mixing rate is based on the light amount setting value and the condition information indicating the driving condition stored in the storage unit, and
  the control unit is further configured to control the driving state of each of the at least two semiconductor light-emitting devices based on the calculated mixing rate.

8. The medical light source device according to claim 7, wherein the storage unit is further configured to store the condition information for each chromaticity of the illumination light.

9. The medical light source device according to claim 7, wherein
  the illumination light is optically connected to a light guiding optical device, and
  the storage unit is further configured to store the condition information for each type of a plurality of types of the light guiding optical device.

10. A method, comprising:
in a medical light source device including a light source part and a control unit, wherein the light source part includes at least two semiconductor light-emitting devices:
  generating, by the light source part, light of specific chromaticity based on mixture of light emitted from each of the at least two semiconductor light-emitting devices,
    wherein the light emitted by a first semiconductor light-emitting device of the at least two semiconductor light-emitting devices has a wavelength different from the light emitted by a second semiconductor light-emitting device of the at least two semiconductor light-emitting devices;
  determining, by the control unit, a mixing rate of the light emitted from each of the at least two semiconductor light-emitting devices, wherein
    the determination of the mixing rate is based on a light amount setting value of illumination light,
    the light amount setting value is based on a user operation, and
    the illumination light corresponds to the generated light; and
  controlling, by the control unit based on the determined mixing rate, a driving state of each of the at least two semiconductor light-emitting devices such that the specific chromaticity is constant regardless of a light amount of the illumination light.

* * * * *